US007980632B2

(12) United States Patent
Pai

(10) Patent No.: US 7,980,632 B2
(45) Date of Patent: Jul. 19, 2011

(54) ARMREST FOR CHAIR

(76) Inventor: Chih-Tang Pai, Banciao (TW)

( * ) Notice: Subject to any disclaimer, the term of this patent is extended or adjusted under 35 U.S.C. 154(b) by 119 days.

(21) Appl. No.: 12/503,203

(22) Filed: Jul. 15, 2009

(65) Prior Publication Data

US 2010/0244531 A1 Sep. 30, 2010

(30) Foreign Application Priority Data

Mar. 27, 2009 (TW) .............................. 98204945 U

(51) Int. Cl.
*A47C 7/54* (2006.01)

(52) U.S. Cl. ................................................. 297/411.36

(58) Field of Classification Search ............... 297/411.2, 297/411.35, 411.36; 248/118, 118.3
See application file for complete search history.

(56) References Cited

U.S. PATENT DOCUMENTS 6,837,545 B1 * 1/2005 Ho .......................... 297/411.36
2008/0036265 A1 * 2/2008 Pan .......................... 297/411.36
2008/0191537 A1 * 8/2008 Oda .......................... 297/411.36
2008/0309140 A1 * 12/2008 Ho .......................... 297/411.36
2009/0096271 A1 * 4/2009 Tsai .......................... 297/411.36

FOREIGN PATENT DOCUMENTS

TW 269800 7/2005
TW 333118 6/2008

* cited by examiner

*Primary Examiner* — Milton Nelson, Jr.

(57) ABSTRACT

An armrest for a chair includes a lower bushing, an upper bushing, and a resilient ring shaped part received in the lower bushing. An engaging portion is formed on an end of the lower bushing, and a side surface of the lower bushing defines a toothed rack hole, a plurality of teeth are formed at two opposite sides of the toothed rack hole. The upper bushing nests the lower bushing therein and defines a through hole corresponding to the toothed rack hole. A supporting is formed on an end of the upper bushing differing from the end of the upper bushing adjacent to the engaging portion. A button opposite to the through hole in the upper bushing is formed on the resilient ring shaped part and protrudes to an outer of the upper bushing from the toothed rack hole and the through hole. An H shaped latching portion is formed on the button and engages with the teeth of the lower bushing.

6 Claims, 7 Drawing Sheets

ARMREST FOR CHAIR

BACKGROUND

Currently, to improve comfort for a user and meet requirements of human engineering, adjusting means have been widely employed in modern chairs to adjust height of armrest according to actual stature of the user.

For example, Taiwan issued patents M333118 and M269800 both disclose a typical armrest for a chair which employs an adjusting means. However, the structure of these armrests is complicated and the great number of parts leads to high complexity in assembling such adjusting means. Accordingly, the material cost and assembling cost are too high. Therefore, there is a desire to develop a new armrest for a chair to overcome above problems.

BRIEF SUMMARY

In order to overcome shortages of high complexity and cost of known armrests used in chairs, the present invention provides a new design.

The present invention provides an armrest for a chair having advantages of simplified structure, reduced cost, and convenience of assembling.

The armrest for a chair provided in the present invention includes a lower bushing, an upper bushing, and a resilient ring shaped part received in the lower bushing. An engaging portion is formed on an end of the lower bushing, and a side surface of the lower bushing defines a toothed rack hole, a plurality of teeth are formed at two opposite sides of the toothed rack hole. The upper bushing nests the lower bushing therein and defines a through hole corresponding to the toothed rack hole. A supporting is formed on an end of the upper bushing differing from the end of the upper bushing adjacent to the engaging portion. A button opposite to the through hole in the upper bushing is formed on the resilient ring shaped part and protrudes to an outer of the upper bushing from the toothed rack hole and the through hole. An H shaped latching portion is formed on the button and engages with the teeth of the lower bushing.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
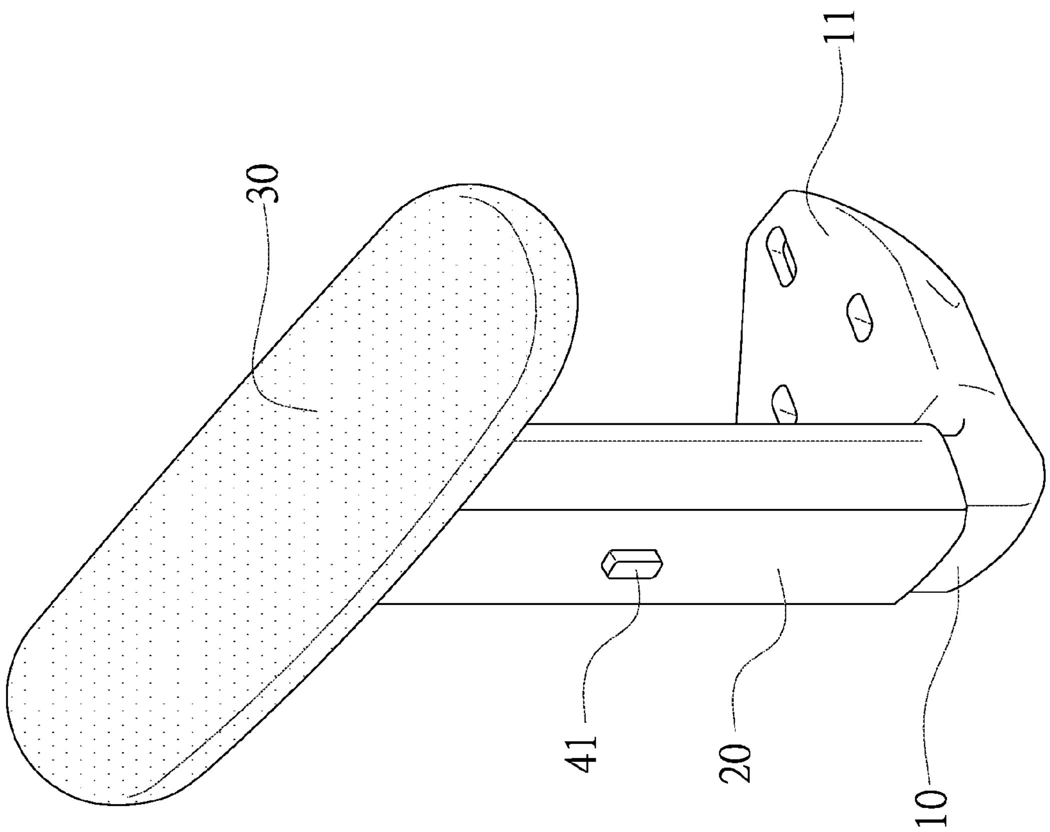
FIG. 1 is an isometric view of an armrest in accordance with the present invention.
Figure 2:
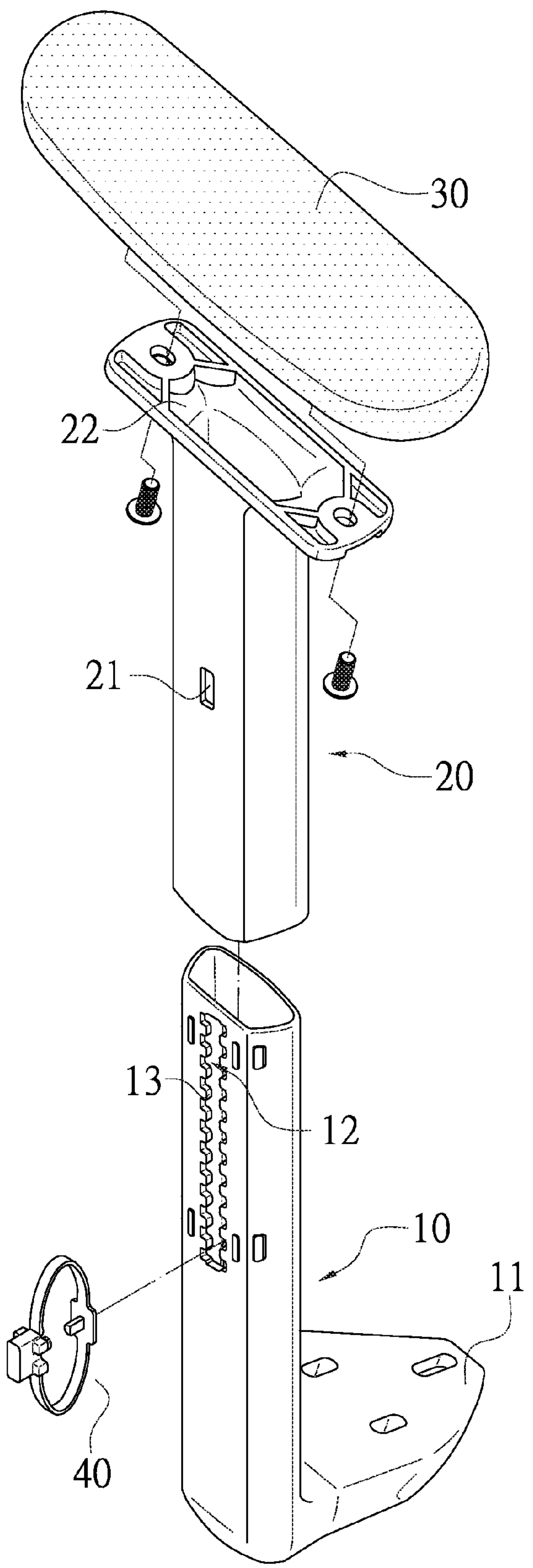
FIG. 2 is an exploded view of the armrest of FIG. 1.
Figure 3:
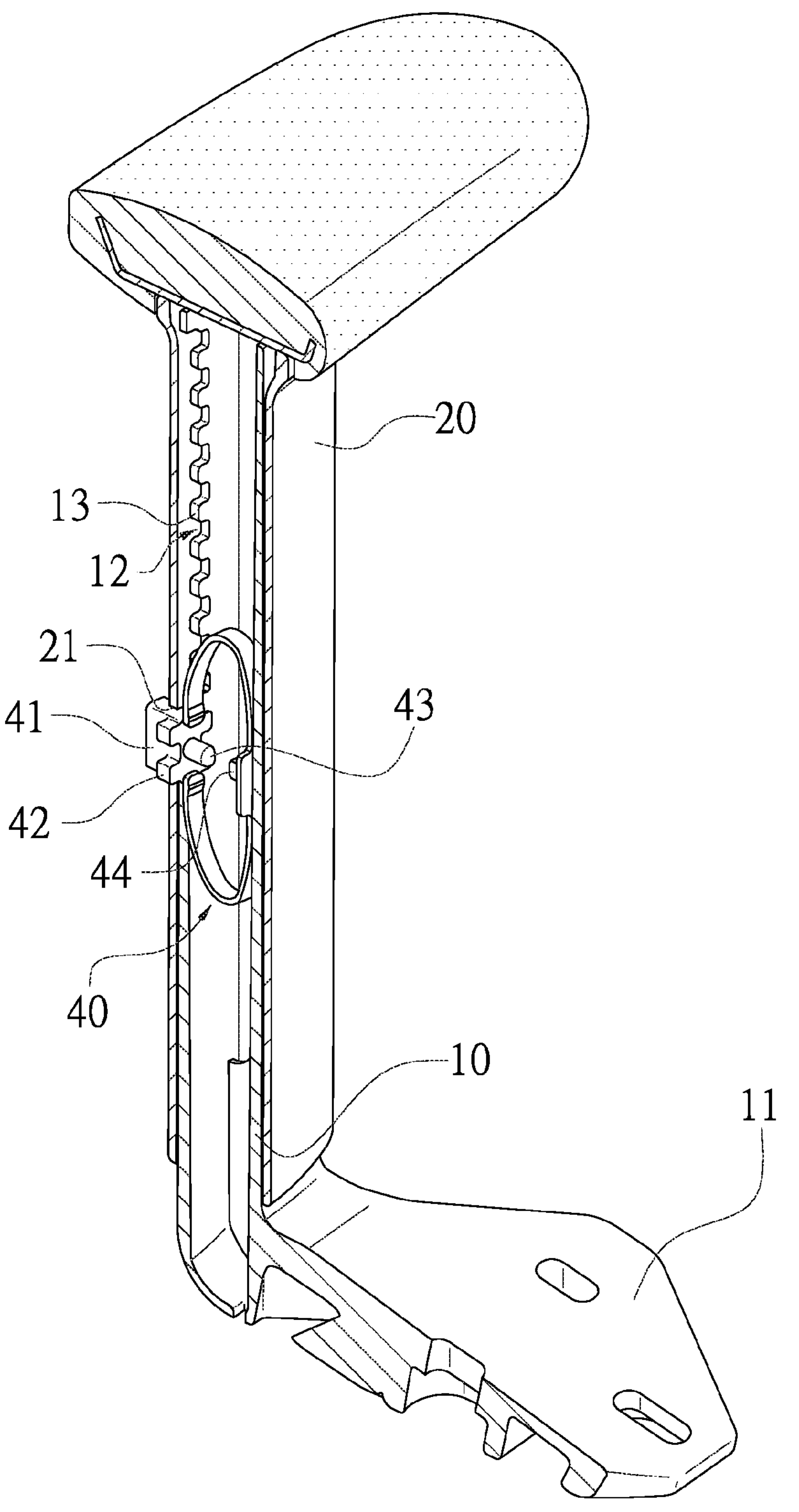
FIG. 3 is a cross sectional view of the armrest of FIG. 1.

As shown in FIGS. 1 to 3, an armrest for a chair according to an embodiment of present invention includes a lower bushing 10, an upper bushing 20, an arm supporting member 30, and a resilient ring-shaped part 40.

An engaging portion 11 for engaging with an armrest support (not shown) is formed on one end of the lower bushing 10. A side surface of the lower bushing 10 defines a toothed rack hole 12 along a longitudinal direction of the lower bushing 10. A plurality of teeth 13 are respectively formed at two opposite sides of the toothed rack hole 12.

The upper bushing 20 nests the lower bushing 10 therein, and defines a through hole 21 corresponding to the toothed rack hole 12. An supporting member 22 is formed on an end of the upper bushing 20 differing from the end of the upper bushing 20 adjacent to the engaging portion 11.

The arm supporting member 30 can be locked, fastened, or latched to the supporting member 22. In the present embodiment, the arm supporting member 30 is fastened to the supporting member 22 with two fasteners (e.g., two screws), and the arm supporting member 30 is a soft pad.

Figure 5:
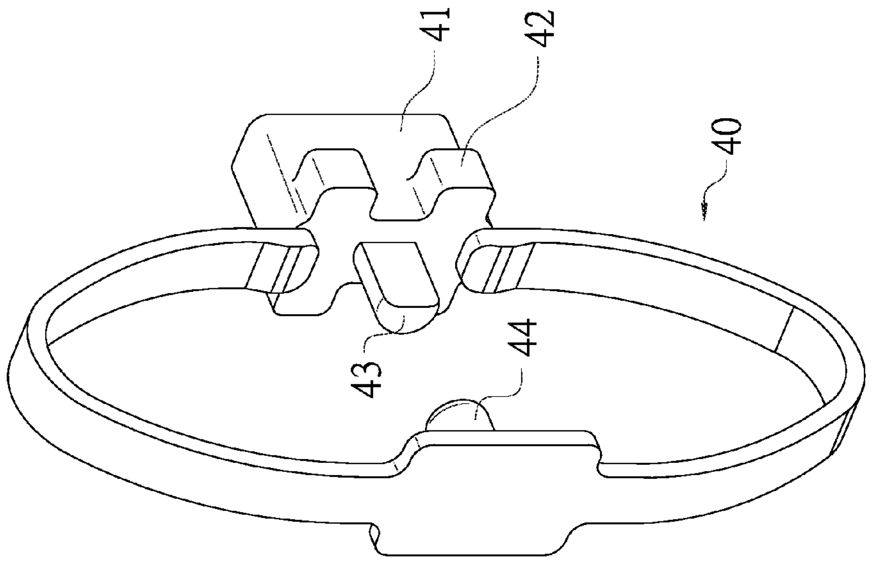
FIG. 5 is similar to FIG. 4, but showing the resilient ring shaped part in different direction.
Figure 4:
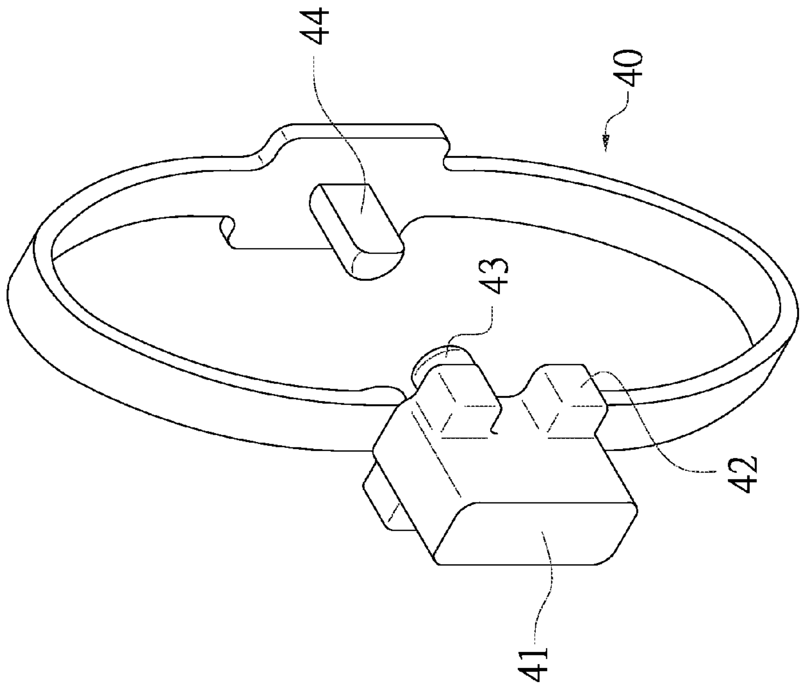
FIG. 4 is an isometric view showing a resilient ring shaped part in accordance with the present invention.

As shown in FIGS. 4 and 5, the resilient ring shaped part 40 comprised of metal or plastic is received in the lower bushing 10. A button 41 opposite to the through hole 21 in the upper bushing 20 is formed on the resilient ring shaped part 40 and protrudes to an outer of the upper bushing 20 from the toothed rack hole 12 and the through hole 21. An H-shaped latching portion 42 is formed on the button 41 for engaging with the teeth 13 of the lower bushing 10. The latching portion 42 includes four teeth extending transversely to two opposite directions. A block 43 extends from the H shaped latching portion 42 to a center of the resilient ring shaped part 40, and a positioning protrusion 44 extends oppositely to the block 43 from an inner portion of the resilient ring shaped part 40.

Figure 6:
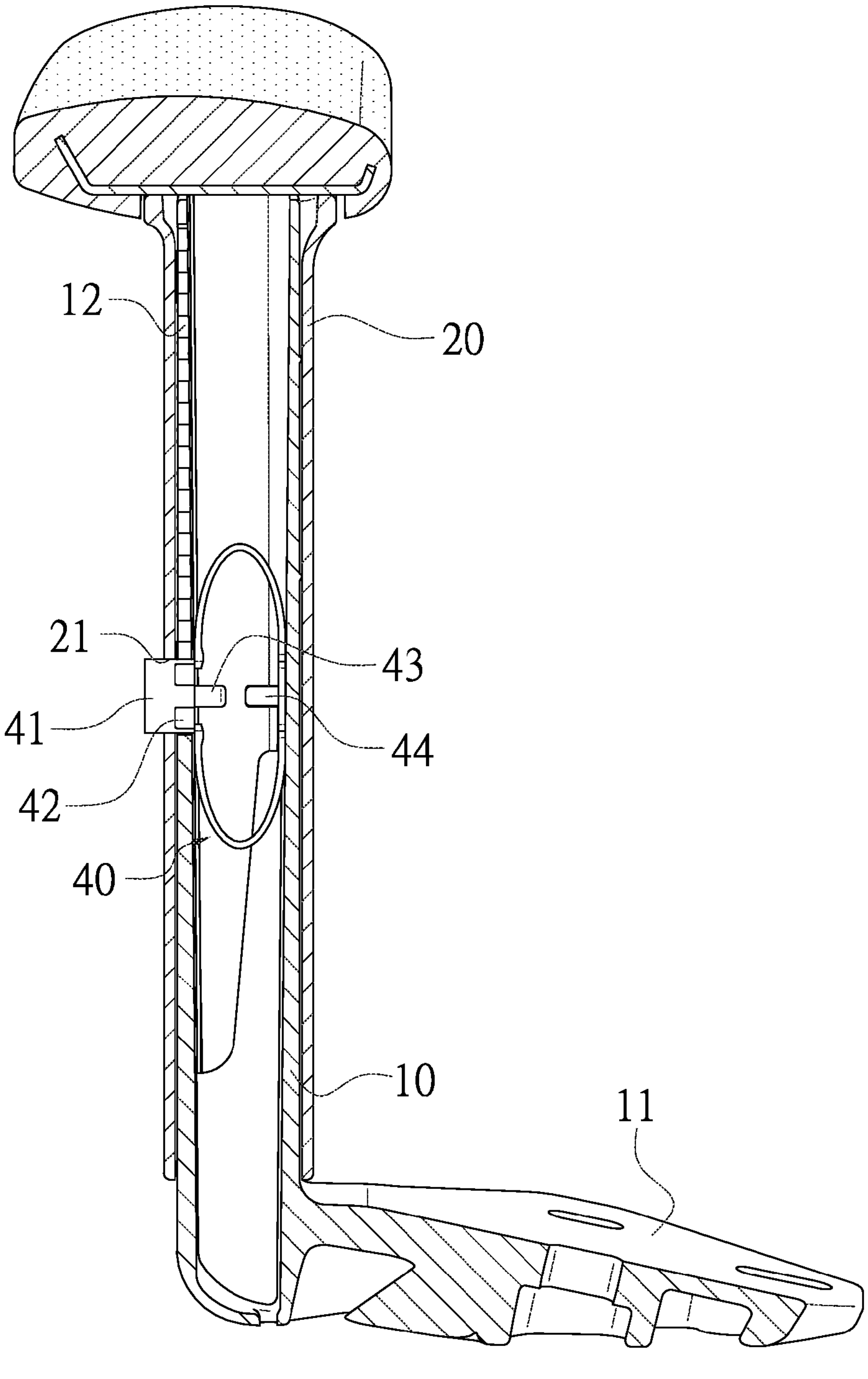
FIG. 6 is a cross sectional view of the armrest of FIG. 1.
Figure 7:
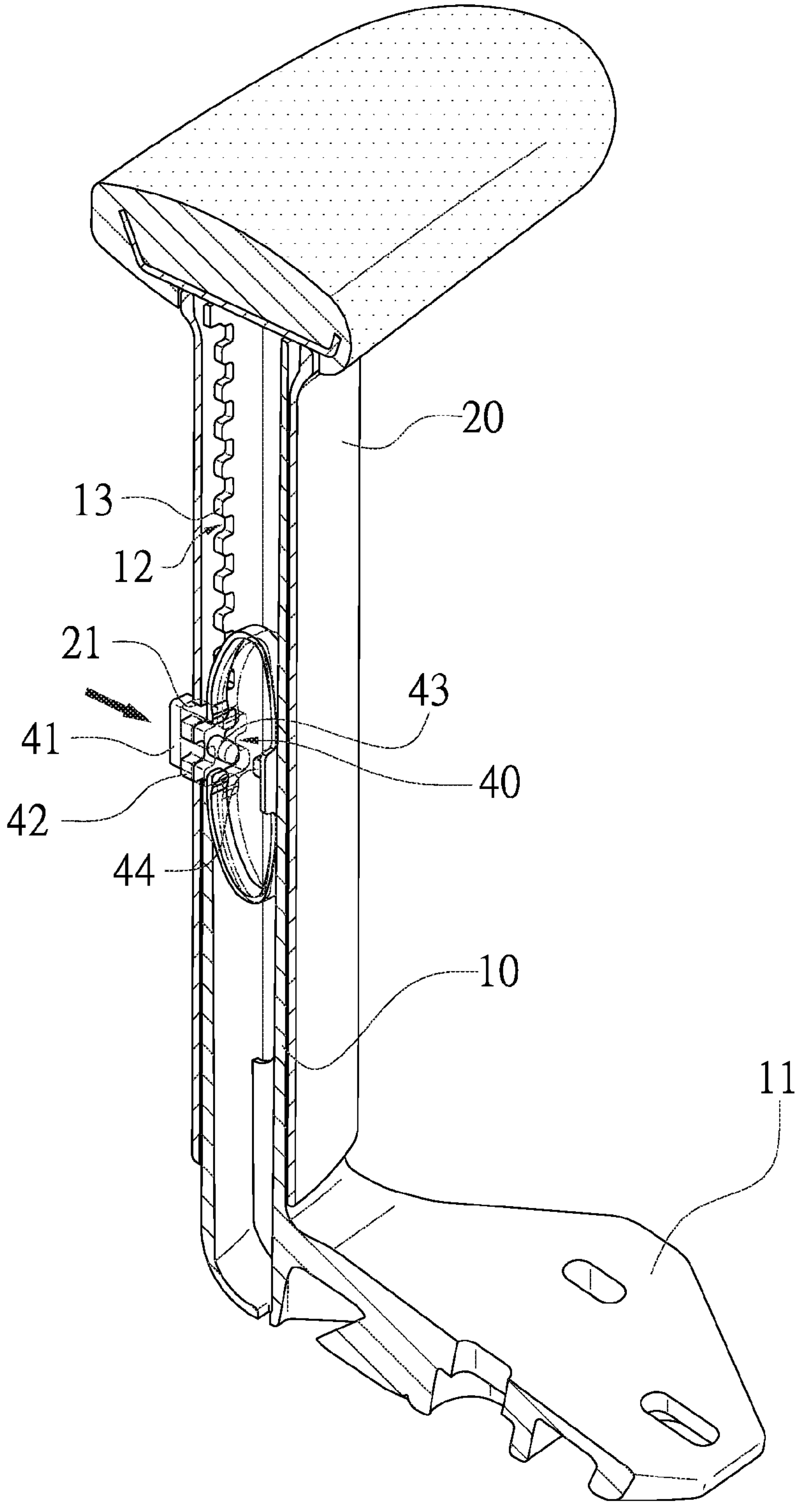
FIG. 7 is a schematic view showing motion of the armrest of FIG. 1.
Figure 8:
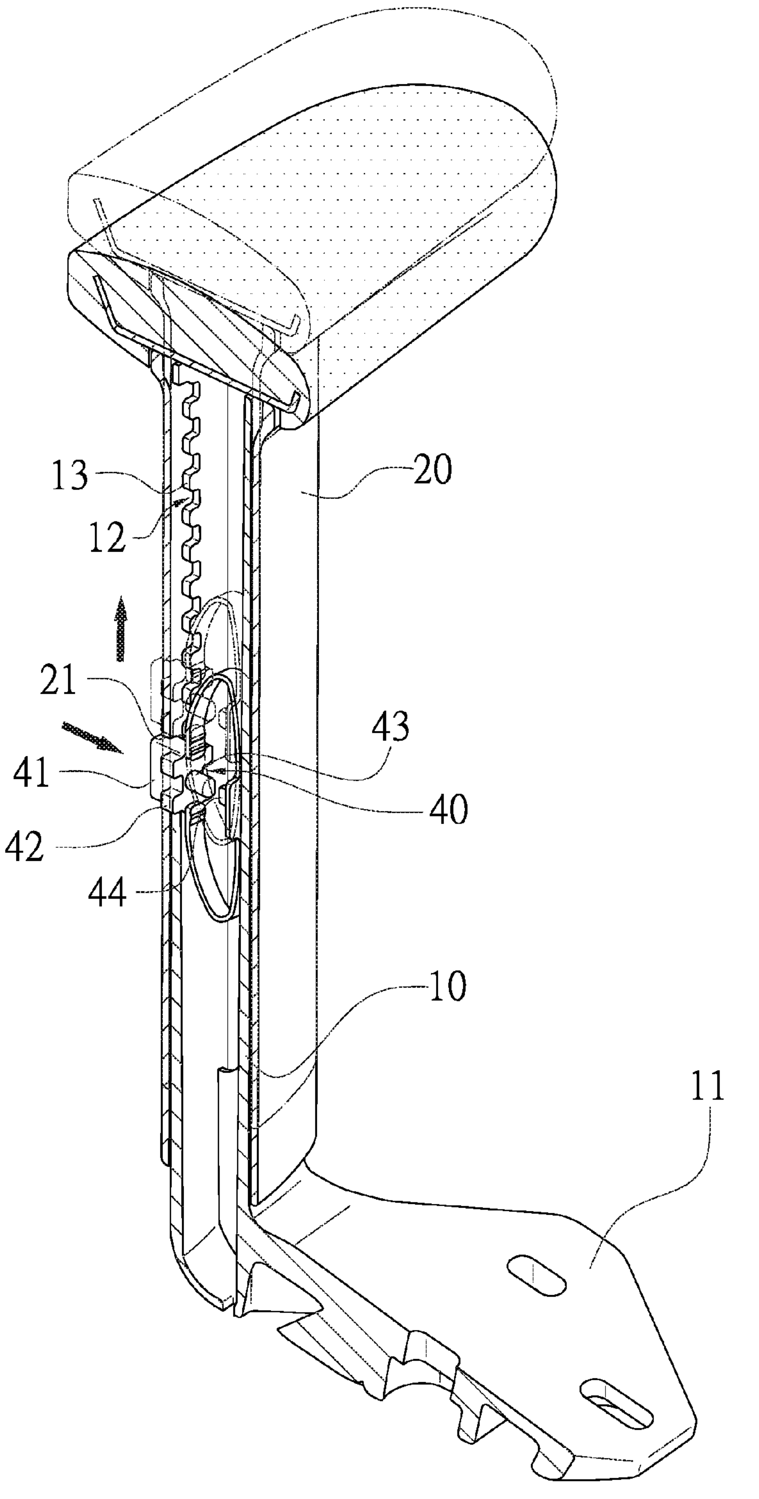
FIG. 8 is similar to FIG. 8, but showing next motion.

To adjust the height of the armrest, as shown in FIGS. 6 to 8, the user need to press down the button 41 such that the resilient ring shaped part 40 to deform in direction toward the positioning protrusion and the H shaped latching portion 42 moved into an inner portion of the lower bushing 10. In this situation, the upper bushing 20 is capable of being moved upwardly or downwardly relative to the lower bushing 10 to adjust the height of the armrest. Further, as the resilient ring shaped part 40 is pressed, the block 43 also moves closing to the positioning protrusion 44; but the resilient ring shaped part 40 can't be further pressed when the positioning protrusion 44 stops the block 43. As such, the block 43 and the positioning protrusion 44 prevent the button from being trapped into the upper bushing 20. In other words, a distance between the block 43 and the positioning protrusion 44 is the retractable distance of the button 41. It is understood that the ring like structure of the resilient ring shaped part 40 improves elastic strength and structure strength thereof. When the armrest is adjusted to the desired height (e.g., elevated relative to the lower bushing 10 as shown in the figures), the button 41 can be released 41 and then the resilient force provided by the resilient ring shaped part 40 would drive the button 41 move to its original position. The H shaped latching portion 42 engages with the teeth again and the upper bushing 20 is latched at desired height relative to the lower bushing 10.

In addition, the teeth 13 in the toothed rack hole can be wave-shaped teeth, or rectangular or polygonal teeth arranged along longitudinal direction of the lower bushing 10. The latching portion 42 of the resilient ring shaped part 40 and the teeth 13 are convexo-concave engaging with each other, and the shape of the latching portion 42 and the teeth 13 is not specially limited. The block 43 and the positioning protrusion 44 can solely exist in the resilient ring shaped part 40 for prevent the button 41 being trapped into the upper bushing 20.

The above description is given by way of example, and not limitation. Given the above disclosure, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. An armrest for a chair, comprising:

a lower bushing with an engaging portion being formed on an end thereof, a side surface of the lower bushing defining a toothed rack hole, a plurality of teeth being formed at two opposite sides of the toothed rack hole;

a upper bushing nesting the lower bushing therein and defining a through hole corresponding to the toothed rack hole, a supporting member being formed on an end of the upper bushing differing from an end of the upper bushing adjacent to the engaging portion; and a resilient ring shaped part received in the lower bushing, a button opposite to a through hole in the upper bushing being formed on the resilient ring shaped part, protruding out of the upper bushing from the toothed rack bole and the through hole, an H shaped latching portion being formed on the button and engaging with the teeth of the lower bushing.

2. The armrest of claim 1, wherein an arm supporting member is formed on an end of the upper bushing, and the arm supporting member is a soft pad.

3. The armrest of claim 1, wherein the resilient ring shaped part is comprised of one of metal and plastic.

4. The armrest of claim 1, wherein a block extends from the H shaped latching portion to a center of the resilient ring shaped part.

5. The armrest of claim 1, wherein a positioning protrusion extends oppositely to the button from an inner portion of the resilient ring shaped part.

6. The armrest of claim 1, wherein a block extends from the H shaped latching portion to a center of the resilient ring shaped part, and a positioning protrusion extends oppositely to the block from an inner portion of the resilient ring shaped part.

* * * * *